United States Patent [19]

Barberet et al.

[11] Patent Number: Plant 5,439

[45] Date of Patent: Apr. 16, 1985

[54] CARNATION NAMED LONDONIE

[75] Inventors: Nicole Barberet; Yves Ducloux, both of Antibes, France

[73] Assignee: Laboratoire de Physiologie Vegetale de La Londe, Antibes, France

[21] Appl. No.: 516,513

[22] Filed: Jul. 25, 1983

[51] Int. Cl.[3] ..... A01H 5/00

[52] U.S. Cl. ..... Plt./73

[58] Field of Search ..... Plt./73

*Primary Examiner*—Robert E. Bagwill

*Attorney, Agent, or Firm*—Charles W. Rummler

[57] ABSTRACT

A new red spray carnation cultivar particularly distinguished by its relatively small flowers, borne on relatively short and rather thin but erect stems, which bloom profusely during the midseason of its Spring and Fall blooming seasons. This plant has a vigorous, upright growth habit with abundant foliage, a very branched habit, and a height averaging about 99 cm. at eight months. A particular advantage of this new plant is that it is very resistant to *Fusarium oxysporum* as observed INRA, Antibes, Alpes-Maritimes, France.

1 Drawing Figure

BACKGROUND OF THE NEW PLANT

This new carnation cultivar is the result of breeding efforts carried on by us at La Londe, Les Maures, France, since 1975, with the object of developing a red spray carnation having good quality of flower and growth habit and a strong resistance to *Fusarium oxysporum* and in this last respect in particular, we believe we have been successful. This new plant originated as a seedling produced from our crossing of selected and individually identified plants growing among our stock of spray carnations maintained at La Londe for breeding purposes. This particular seedling was selected by us for propagation and test because it appeared to be the best of the seedlings produced by the said crossing, especially resistant to *Fusarium oxysporum* disease, and the discovery plant was reproduced by us at La Londe, by means of cuttings. The resulting plants appeared to be so favorable that propagation was carried on for several years through many generations, which demonstrated that the distinctive and most desirable characteristics of the discovery plant were fully retained from generation to generation and appeared to be firmly fixed.

DESCRIPTION OF THE DRAWING

Our new carnation cultivar is illustrated by the accompanying photographic drawing which shows, in full color, a typical arrangement of buds and flowers in various stages of opening, the colors shown being as nearly true to those specified as is reasonably possible to obtain by conventional photographic procedures.

DESCRIPTION OF THE NEW PLANT

The following is a detailed description of our new carnation discovery based upon observations of greenhouse grown plants at La Londe, France, in the Spring of 1983, the color designations being specified according to The R.H.S. Colour Chart published by The Royal Horticultural Society of London, England.

THE PLANT

Origin: Seedling.

Parentage:

*Seed parent.*—Stock Plant No. 397 M R.

*Pollen parent.*—Stock Plant No. 72 M R 4. These unnamed varieties of spray carnations are individually identified in our permanent records and are maintained for breeding purposes in our collection of carnation plants at La Londe, France.

Classification:

*Botanic.*—*Dianthus caryophyllus.*

*Commercial.*—Spray Carnation.

Form: Bush; erect and with at least four stems emitted near the ground.

Height: Averages about 99 cm. at eight months.

Main stem:

*Length.*—Less than 15 cm. due to pinching.

Branching character: Very branched.

Growth habit: Vigorous, upright and rather rigid.

Foliage:

*Quantity.*—Abundant.

*Number of leaves.*—At least 120.

*Leaf size.*—Average — About 12 cm. long and 7 mm. in width at the seventh node.

*Leaf shape.*—Linear with curved margins.

*Texture.*—Leathery.

*Color.*—Upper side — 189A and 189B. Under side — 189A and 189B.

*Ribs and veins.*—Hardly noticeable.

*Rachis.*—Hardly noticeable.

THE BUD

Form: Long ovoid.

Size: Medium.

*Diameter.*—Averages about 1.2 cm.

*Length.*—Averages about 3.2 cm.

Opening rate: About normal for carnations.

Color of petals:

*When sepals first divide.*—Same as at full bloom.

*When petals begin to unfurl.*—Same as at full bloom.

Sepals:

*Number.*—5 To 6.

*Shape.*—Joined at lower part and upper part being generally acute and sharply pointed at its apex. The sepals continue to stand up when the flower is open.

*Color.*—Inside — Greenish white. Outside — 138B and 144C.

*Striae.*—Longitudinal.

Calyx:

*Shape.*—Rather cylindrical and long to bell-shaped at the upper end.
*Splitting.*—The calyx does not split.
*Aspect.*—Smooth.

Flower stem:
*Length.*—About 55 cm.
*Character.*—Erect and rather thin.
*Color.*—189A and 189B.

THE FLOWER

Blooming habit: Recurrent, blooming profusely during midseason of Spring and Fall.

Size of bloom: Small.
*Diameter.*—Averaging about 5.5 cm.
*Depth.*—Averaging about 5.5 cm.

Borne: In cluster.

Shape:
*When bloom first opens.*—High centered.
*When bloom matures.*—Dome shaped.

Petalage:
*Number of petals.*—Averaging about 50.
*Arrangement.*—Imbricated.
*Form.*—Fan-shaped with wavy or undulated margin.
*Texture.*—Soft.
*Appearance.*—Satiny.
*Color.*—Outer Petal: Body — 46B. Base — Greenish white. Reverse side — 45C. Inside Petal: Body — 46B. Base — Greenish white. Reverse side — 45C.

Flower stem:
*Length.*—About 55 cm. (cut at tenth node).

*Character.*—Upright and of good strength.
*Color.*—189A and 189B.

Fragrance: Slightly perceptible.

Persistence: The petals hang on and dry.

Lasting quality:
*As cut flower.*—At least ten days in vase keeping.

REPRODUCTIVE ORGANS

Stamens:
*Number.*—15 To 28.
*Arrangement.*—Around the pistils.
*Anthers.*—Size: Less than 4 mm. Color: Whitish.
*Filaments.*—Color — Whitish.

Pistils:
*Number.*—3 To 5.
*Styles.*—Color — White.
*Stigmas.*—Color — Pinkish white.

Character of ovaries: Ribbed surface and with chlorophyll.

This new red spray carnation most resembles the variety "Lonsoury" and differs from "Lonsoury" by having less serration of the petals, a shorter stem and a more abundant foliage. Also, it is more resistant to *Fusarium oxysporum* than "Lonsoury".

We claim:

1. A new and distinct spray carnation, substantially as herein shown and described, characterized by the bright red color of its small blooms borne on thin, erect stems, a vigorous growth habit with abundant foliage, and a habit of blooming profusely during its Spring and Fall flowering seasons.

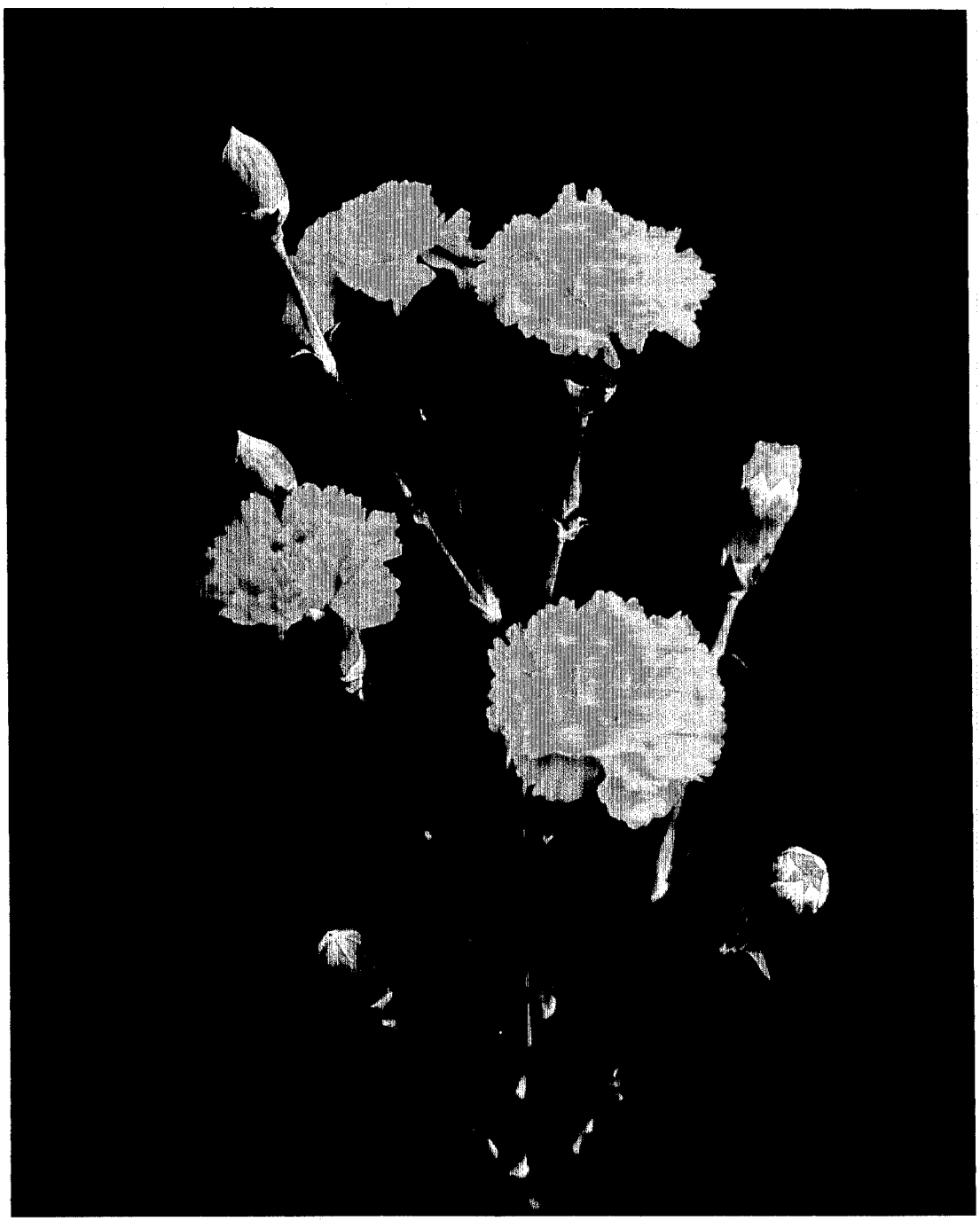

* * * * *